US011911463B2

(12) United States Patent
Dochniak

(10) Patent No.: US 11,911,463 B2
(45) Date of Patent: Feb. 27, 2024

(54) TOPICAL HYPER-ALLERGENIC COMPOSITION AND METHOD OF TREATING USING THE SAME

(71) Applicant: Michael J. Dochniak, St. Paul, MN (US)

(72) Inventor: Michael J. Dochniak, St. Paul, MN (US)

(*) Notice: Subject to any disclaimer, the term of this patent is extended or adjusted under 35 U.S.C. 154(b) by 654 days.

(21) Appl. No.: 16/513,334

(22) Filed: Jul. 16, 2019

(65) Prior Publication Data

US 2021/0015912 A1  Jan. 21, 2021

(51) Int. Cl.
| | |
|---|---|
| A61K 39/35 | (2006.01) |
| A61K 39/39 | (2006.01) |
| A61P 35/04 | (2006.01) |
| A61K 9/00 | (2006.01) |
| A61K 39/00 | (2006.01) |

(52) U.S. Cl.
CPC ............ *A61K 39/35* (2013.01); *A61K 9/0014* (2013.01); *A61K 39/39* (2013.01); *A61P 35/04* (2018.01); *A61K 2039/54* (2013.01); *A61K 2039/55516* (2013.01)

(58) Field of Classification Search
CPC ...... A61K 39/35; A61K 9/0014; A61K 39/39; A61K 2039/54; A61K 2039/55516; A61P 35/04
See application file for complete search history.

(56) References Cited

U.S. PATENT DOCUMENTS

| | | |
|---|---|---|
| 8,071,106 B2 | 12/2011 | Mrue |
| 9,119,974 B2 | 1/2015 | Al-Qahtani |
| 9,950,063 B2 | 4/2018 | Reed et al. |
| 10,238,686 B1 | 3/2019 | Ganga, Sr. |
| 2004/0175757 A1 | 9/2004 | Olsen et al. |

OTHER PUBLICATIONS

Banerjee et al. Unique and shared IgE epitopes of Hev b 1 and Hev b 3 in latex allergy. Molecular Immunology vol. 37, Issues 12-13, Sep. 1, 2000, pp. 789-798.*
Michael J Dochniak, Rubber Elongation Factor and Natural Allergy-Oncology, 2016, Open Access 2: 027, BAOJ Cancer Research & Therapy, Wilmington Delaware, USA.
Karine Berthlot, et al., Rubber Elongation Factor [REF], a major allergen component in Hevea Brasiliensis latex has amyloid properties, 2012, PLOS One; 7[10]: e 48065.
Judith Schwartzbaum, et al., (2012) Association between prediagnostic IgE levels and risk of glioma, 2012, Journal of the National Cancer Institute; 104[16]: 1251-1259.
Domenico Ribatti, et al., Mast cells, angiogenesis, and tumour growth. 2012, Biochimica et Biophysica Acta (BBA)—Molecular Basis of Disease; 1822(1): 2-8.
Ravi K. Upadhyay, Plant Latex: A natural source of pharmaceuticals and pesticides, 2011, International Journal of Green Pharmacy; 5(3).
Jenson-JarolimE, et al., AllergoOncology: the role of IgE-mediated allergy in cancer, 2008, Allergy; 63[10]: 1255-1266.
Rob C. Aalberse, Assessment of allergen cross reactivity: Commentary, 2007, Clinical and Molecular Allergy; Open Access 5(2).
Product Information—Alhydrogel® adjuvant 2%, Aluminium hydroxide gel from InvivoGen, San Diego, CA. (pp. 1-5) (May 27, 2019).
Product Information—rHev-b allergens, Phadia Immunology Reference Laboratory, Thermo Fischer Scientific, Waltham, MA USA, 16 pages, (2012).

* cited by examiner

*Primary Examiner* — Jeffrey Stucker
(74) *Attorney, Agent, or Firm* — Allison Johnson, P.A.; Allison Johnson

(57) ABSTRACT

A topical hyper-allergenic composition that includes a first protein that exhibits amyloid-β structure and immunogenicity in humans, a second protein that exhibits immunogenicity in humans, an immunologic adjuvant, and a carrier.

3 Claims, No Drawings

TOPICAL HYPER-ALLERGENIC COMPOSITION AND METHOD OF TREATING USING THE SAME

BACKGROUND

The invention relates to formulating compositions having hyper-allergenic properties and methods of treating metastatic cancer using the same.

The predominant reason that cancer is so serious is its ability to spread in the body. Cancer cells can spread to a variety of areas: locally by moving to nearby normal tissue, regionally by moving to nearby lymph nodes, tissues, and organs, and distantly by moving to distant parts of the body. The process by which cancer cells spread to other parts of the body is called metastasis. When this happens, the cancer is called metastatic.

Metastatic cancer spreads through the body in a series of steps. These steps include: growing into, or invading, nearby normal tissue; moving through the walls of nearby lymph nodes or blood vessels; traveling through the lymphatic system and bloodstream to other parts of the body; stopping in small blood vessels at a distant location, invading the blood vessel walls, and moving into the surrounding tissue; growing in this tissue until a tiny tumor forms; and causing new blood vessels to grow, which creates a blood supply that allows the tumor to continue growing.

Most types of cancer have four stages. Stage I usually means that a cancer is relatively small and contained within the organ it started. Stage II usually means that the tumor is larger than in stage I, but the cancer has not started to spread into the surrounding tissues. Stage III usually means the cancer is increasing in size and may have started to spread into surrounding tissues. Stage IV (metastatic cancer) means the cancer has spread from where it started to another body organ.

A variety of procedures for treating cancer exist. Many of these treatments require expensive medical equipment and an experienced professional such as a doctor or a nurse to carry out the treatment on the cancer patient. Many of these treatments also require the use of needles and painful pin pricks.

Cancer immunotherapy is a form of treatment that uses the power of the body's innate and humoral immune system to inhibit and eliminate cancer. Allergy-oncology utilizes humoral immunity to inhibit tumor grown and metastasizing. Repeated exposure to allergens induces the human body to form B-cells, class-E immunoglobulin (IgE) antibodies, and IgE-primed effector cells, which bind to the allergen to begin the process of elimination and removal. Suppression of metastatic cancer is suspected with IgE antibodies in that they are extremely biologically active despite being present in relatively low concentrations in the bloodstream, i.e., approximately one-thousandth of a percent. B-cells produce IgE antibodies that bind to high-affinity receptors on the surface of effector cells (e.g., mast cells, basophils, and eosinophils) to provide IgE-primed effector cells. The IgE-primed effector cells bind to allergens and endogenous proteins having structure homology to expedite their removal.

Skin contains elements of humoral immunity (i.e., adaptive immunity), which allows it to be sensitive to allergens. Although methods of testing an individual's allergic response to various allergens using a pin pricks, intradermal injections, subcutaneous injections and intramuscular injections exist, these methods elicit a relatively quick and short response from the individual's immune system and the individual's exposure to the allergen is short-lived.

There is a need for a composition that induces a hyper-allergenic response in an individual and induces the individual to produce IgE-primed effector cells that bind endogenous-proteins associated with metastatic cancer. There is also a need for a cancer treatment therapy that can be applied without the use of needles and syringes.

SUMMARY

In one aspect, the invention features a topical hyper-allergenic composition that includes a first protein that exhibits amyloid-β structure and immunogenicity in humans, a second protein that exhibits immunogenicity in humans, an immunologic adjuvant, and a carrier. In one embodiment, the composition induces the production of IgE-primed effector cells. In some embodiments, the IgE-primed effector cells bind to endogenous proteins associated with metastatic cancer. In another embodiment, the composition induces the production of memory B cells. In other embodiments, the composition induces the production of class E immunoglobulin (IgE) antibodies. In another embodiment, the composition is substantially free of growth factor.

In one embodiment, the first protein is selected from the group consisting of purified native protein, recombinant protein, and combinations thereof. In other embodiments, the first protein is derived from *Hevea brasilensis*. In some embodiments, the first protein includes Hev b-1.

In other embodiments, the immunologic adjuvant comprises a granulocyte macrophage colony-stimulating factor.

In some embodiments, the immunologic adjuvant forms an association with at least one of the first and second proteins.

In one embodiment, the second protein is a non-amyloidal protein.

In another aspect, the invention features a method of treating cancer in a patient, the method including applying a composition to the skin of the patient, the composition including a first protein that exhibits amyloid-β structure and immunogenicity in humans, a second protein that exhibits immunogenicity in humans, an immunologic adjuvant, and a carrier. In one embodiment, the applied composition induces the production of IgE-primed effector cells, and wherein the IgE-primed effector cells bind to the patient's endogenous proteins associated with metastatic cancer. In another embodiment, the method further includes massaging the composition into the skin.

In other aspects, the invention features a method of treatment that includes determining at least one allergy of a cancer patient, and applying a hyper-allergenic composition to the skin of the patient, the hyper-allergenic composition including a first protein that exhibits amyloid-β structure and immunogenicity in the patient, a second protein that exhibits immunogenicity in the patient, an immunologic adjuvant, and a carrier. In one embodiment, the hyper-allergenic composition is substantially free of growth factor.

In another aspect, the invention features a package that includes a container, and the topical hyper-allergenic composition disclosed herein disposed in the container.

The hyper-allergenic composition (e.g., a cream), when applied topically, induces the formation of class-E immunoglobulins (IgE) and IgE-primed effector cells when in contact with the skin of an individual. Topical application of the hyper-allergenic composition also provides a useful method of treating or preventing cancer.

Other features and advantages will be apparent from the following description of the preferred embodiments and from the claims.

Glossary

In reference to the invention, these terms have the meanings set forth below:

The term "antigen" means a foreign substance that elicits an immune response when in contact with skin.

The term "allergen" means an exogenous protein or antigen that elicits an immunoglobulin-E response when in contact with skin.

The term "immunogenicity" means the ability of a substance to provoke an immune response in the body of a patient.

The phrase "immunologic adjuvant" means a substance that that potentiates the immune response to the antigen, modulates the immune response to the antigen, or a combination thereof.

The term "hyper-allergenic" means a substance that induces the formation of class-E immunoglobulins (IgE) and IgE-primed effector cells.

DETAILED DESCRIPTION

The topical hyper-allergenic composition includes a first protein that exhibits amyloid-β structure and immunogenicity in humans, a second protein that exhibits immunogenicity in humans, an immunologic adjuvant, and a carrier. In use, the hyper-allergenic composition is applied to the surface of an individual's skin and rubbed into the skin. The presence of the hyper-allergenic composition on the individual's skin provides an extended period of time during which the body's immune system is exposed to the immunogenic agents (i.e., the first protein, the second protein, and the immunologic adjuvant). The hyper-allergenic composition induces an atopic response in an individual (e.g., a cancer patient), a specific allergic response in an individual, or both an atopic response and a specific allergic response in an individual. Without wishing to be bound by theory, the present inventor believes that the immunogenic agents used in the topical composition can induce a negative feedback loop wherein the formation of IgE-primed effector cells inhibit the expression of endogenous proteins associated metastasizing cells.

The specific amounts of protein allergen and immunologic adjuvant for any particular individual will depend upon a variety of factors including the age, body weight, general health, sex, diet, time of administration, rate of excretion, allergen-immunologic adjuvant combination, and the severity of the cancer in the individual undergoing therapy. Unit dosage forms include a predetermined amount of allergen(s) and immunologic adjuvant(s) composition. A "unit dosage form" includes a physically discrete unit suitable as a unitary dosage for a human subject, each unit containing a predetermined quantity of allergen and immunologic adjuvant in an amount sufficient to produce the desired effect.

Protein Allergens

The hyper-allergenic composition includes at least two protein allergens that exhibit immunogenicity in humans. The protein allergens can be any purified native protein or recombinant protein that exhibits an allergenic response in a human. The first protein allergen exhibits amyloid-β structure (β-sheet) and produces IgE-primed effector cells that cross-react with endogenous proteins based on factors including, e.g., structure homology, epitope similarity, and combinations thereof.

One useful class of protein allergens that exhibit amyloid-β structure is the class of protein allergens that are derived from *Hevea brasiliensis* (i.e., Hev) and exhibit amyloid-β structure. Analysis of the latex in *Hevea brasiliensis* indicates that there are about 200 dissimilar proteins found therein. From 50 to 60 of those proteins are suspected allergens. The World Health Organization—International Union of Immunological Societies has assigned names to 13 of these allergens (e.g., Hev-b 1-13). A preferred allergen from *Hevea brasiliensis* is Hev-b 1. Hev-b 1 is an amyloidal protein (i.e., a protein allergen that exhibits amyloid-β structure) that is water-insoluble protein and has a molecular weight of 14.6 KDa. The hyper-allergenic composition includes at least 0.001% by weight, no greater than 99% by weight, from 0.1% by weight to 30% by weight, from 0.5% by weight to 20% by weight, or even from 1% by weight to 10% by weight of the first protein allergen based on the total weight of the hyper-allergenic composition.

Useful non-amyloidal allergens derived from *Hevea brasiliensis* include, e.g., Hev-b 2 (endo-β-1,3-glucanase); Hev-b 3 (small rubber-particle protein); Hev-b 4 (microhelix component); Hev-b 5 (acidic latex protein); Hev-b 6.01 (prohevein, hevein preprotein); Hev-b 6.02 (hevein); Hev-b 6.03 (prohevein C-terminal fragment); Hev-b 7.02 (patatin homologue from C-serum); Hev-b 8 (latex profilin); Hev-b 9 (latex enolase); Hev-b 10 (Mn-superoxide dismutase); Hev-b 11 (class I endochitinase); Hev-b 12 (lipid transfer protein); and Hev-b 13 (latex esterase).

Useful second protein allergens include, e.g., non-amyloidal allergens including the non-amyloidal allergens of *Hevea brasiliensis* discussed above including, e.g., Hev-b 2, Hev-b 3, Hev-b 4, Hev-b 5, Hev-b 6, Hev-b 7, Hev-b 8, Hev-b 9, Hev-b 10, Hev-b 11, Hev-b 12, and Hev-b 13.

Other useful second protein allergens include, e.g., pollen allergens (e.g., tree, herb, weed and grass pollen allergens), insect allergens (e.g., inhalant, saliva and venom allergens, e.g. cockroach, midge and house dust mite allergens and hymenoptera venom allergens), animal hair allergens, animal dander allergens (e.g. dog, cat, horse, rat, mouse, and rabbit), food allergens and combinations thereof.

Specific protein allergens include, e.g., protein allergens of the following genera: *Dermatophagoides, Felis, Ambrosia, Lolium, Cryptomeria, Alternaria, Alder, Betula, Blomia, Quercus, Olea, Artemisia, Plantago, Parietaria, Canine Blattella; Apis, Cupressus, Thuya, Chamaecyparis, Periplaneta, Agropyron, Secale, Triticum, Cynorhodon, Juniperus, Dactylis, Festuca, Poa, Lolium, Avena, Holcus, Anthoxanthum, Arrhenatherum, Agrostis, Phleum, Phalaris, Paspalum*, and *Sorghum*.

Examples of various known protein allergens derived from some of the above-identified genera include: *Betula* (*verrucosa*) Bet v I; Bet v II; *Blomia* Blo 1 1; Blo t III; Blo t V; Blo t XII; *Cynorhodon* Cyn d I; *Dermatophagoides* (*pteronyssinus* or *farinae*) Der p I; Der p II; Der p III; Der p VII; Der f I; Der f II; Der f III; Der f VII; *Lollium* (*perenne*) Lol p I; Lot p II; Lol p III; Lot p IV; Lol p IX (Lol p V or Lol p Ib); *Cryptomeria* (*japonica*) Cry j I; Cry j II; Jun s I and Jun v I; *Canis* (*familiaris*) Can f I; Can f II; *Juniperus* (*sabinoides* or *virginiana*) Jun s I; Jun v I; *Juniperus* (*ashei*) Jun a I; Jun a II; *Dactylis* (*glomerata*) Dae g I; Dae g V; *Poa* (*pratensis*) *Poa* p I; PhI p I; PhI p V; PhI p VI and *Sorghum* (*halepensis*) Sor h I, and combinations thereof;

*Arachis hypogea* (Ara h 1-Ara h 11): Ara h 1, a Cupin (Vicillin-type, 7S globulin) of 64 kDa; Ara h 2, a Conglutin (2S albumin) of 17 kDa; Ara h 3, a Cupin (Legumin-type, 11S globulin, Glycinin) of 60 kDa; Ara h 4, a Cupin (Legumin-type, 11S, Glycinin) of 37 kDa; Ara h 5, a Profilin of 15 kDa; Ara h 6, a (2S albumin) of 15 kDa; Ara h 7, a Conglutin (2S albumin) of 15 kDa; Ara h 8, a Pathogenesis-related protein, PR-10 of 17 kDa; Ara h 9, a Nonspecific lipid-transfer protein 1 of 9.8 kDa; Ara h 10, a 16 kDa oleosin, and Ara h 11, a 14 kDa oleosin, and combinations thereof;

Cat allergens (i.e., Felis domesticus) include, e.g., Fel d 1 an Uteroglobin of 14 and 4 kDa; Fel d 2 an Albumin of 69 kDa; Fel d 3 a Cystatin of 11 kDa; Fel d 4, a Lipocalin of 22 kDa; Fel d 5, an Immunoglobulin A of 400 kDa; Fel d 6, a Immunoglobulin M of 800-1000 kDa; Fel d 7, a von Ebner gland protein of 17.5 kDa; Fel d 8 a Latherin-like protein of 24 kDa, and combinations thereof;

Grass allergens of the species *Phleum pretense* include, e.g., Phl p 1, a Beta-expansin of 27 kDa; Phl p 2, a Grass group II/III of 10-12 kDa; Phl p 4, a protein of 55 kDa, Phl p 5 of 32 kDa, Phl p 6 of 11 kDa, Phl p 7 a calcium binding protein of 6 kDa, Phl p 11, Ole e 1-related protein of 20 kDa, Phl p 12 a profilin of 14 kDa and Phl p 13, polygalacturonase of 55 kDa, and combinations thereof;

Grass allergens of the genus *Phragmites* include, e.g., *P. australis* and *P. communis*. Allergens of *Phragmites* include An Expansin of 30 kDa, a protein belonging to the group 4 of grasses of 60 kDa, a ribonuclease of 35 kDa, a profilun of 14 kDa, and a polygalacturonase, and combinations thereof;

Ragweed (*Ambrosia*) allergens of the species *Ambrosia artemisiifolia*, *A. psilostachya*, and *A. trifida*. F include, e.g., allergens of *Ambrosia artemisiifolia* (e.g., Amb a 1-Amb a 10 (e.g., Amb a 1 a Pectate lyase of 38 kDa, Amb a 2 a Pectate lyase of 38 kDa, Amb a 3 a Plastocyanine of 11 kDa, Amb a 4 a Defensin like protein of 30 kDa, Amb a 5, of 5 kDa, Amb a 6 a lipid-transfer protein of 10 kDa, Amb a 7 a Plastocyanin of 12 kDa, Amb a 8 a Profilin of 14 kDa, Amb a 9 a Polcancin of 10 kDa, and Amb a 10, a Polcalcin-like protein of 18 kDa), and Allergens of *A. psilostachya* (Amb p 5), and combinations thereof;

Nut allergens include, e.g., peanut allergens (e.g., rAra h 1, rAra h 2, rAra h 3, rAra h 8 PR-10, and rAra h 9 LTP), brazil nut allergens (e.g., rBer e 1), hazelnut or filbert allergens (e.g., rCor a 1 PR-10, rCor a 8 LTP, nCor a 9, rCor a 14), walnut allergens (e.g., rJug r 1, rJug r 3 LTP), cashew allergens, pistachio allergens, pecan allergens, tree nut allergens (e.g., allergens from cashew nut, walnut, hazelnut, brazil nut), and combinations thereof;

Vertebrate animal allergens include, e.g., avian allergens (e.g., egg allergens (e.g., nGal d 1 Ovomucoid, n Gal d 2 Ovalbumin, nGal d 3 Conalbumin, and egg white complete allergen), mammalian allergens (e.g., milk allergens (e.g., nBos d 4 alpha-lactalbumin, nBos d 5 beta-lactoglobulin, nBos d 8 Casein, and nBos d Lactoferrin), fish allergens (e.g., rCyp c 1, rGad c 1, cod complete allergen, white fish allergens, and pink fish allergens), and combinations thereof;

Invertebrate animal allergens include, e.g., crustacean allergens, such as shrimp allergens (e.g., rPen a 1 tropomyosin, shrimp complete allergen), insect allergens (e.g., bee sting venom allergen, wasp sting venom allergen, and mosquito bite allergen) and combinations thereof;

Useful protein allergens are commercially available from a variety of sources including, e.g., Thermo Fisher Scientific, Phadia, U.S. Inc.

The hyper-allergenic composition includes at least 0.001% by weight, no greater than 99% by weight, from 0.1% by weight to 30% by weight, from 0.5% by weight to 20% by weight, or even from 1% by weight to 10% by weight of the second protein allergen based on the total weight of the hyper-allergenic composition.

The hyper-allergenic composition includes at least 0.001% by weight, no greater than 99% by weight, from 0.1% by weight to 30% by weight, from 0.5% by weight to 20% by weight, or even from 1.0% by weight to 10% by weight total protein allergen based on the total weight of the hyper-allergenic composition.

Immunologic Adjuvant

The hyper-allergenic composition also includes at least one immunologic adjuvant. The immunologic adjuvant is a substance that potentiates the immune response(s) to the antigen, modulates the immune response to the antigen, or a combination thereof. The immunologic adjuvant can have a variety of effects on an antigen-specific immune response including, e.g., accelerating, prolonging, or enhancing an antigen-specific immune response, and combinations thereof, when used in combination with an antigen. Useful classes of immunologic adjuvants include, e.g., inorganic immunologic adjuvants, organic immunologic adjuvants, hydrophobic immunologic adjuvants, hydrophilic immunologic adjuvants, mineral salts (e.g., aluminum salts (e.g., aluminum hydroxide and aluminum phosphate), calcium phosphate, and combinations thereof), oil emulsions, surfactant-based compositions (e.g., MF59 microfluidized detergent stabilized oil in water emulsion), QS21 purified saponin, QS21 mimetics, AS02 [SBAS2] (oil-in-water emulsion+MPL+QS-21), Montanide ISA-51 and ISA-720 (stabilized water-in-oil emulsion), particulate adjuvants, e.g., virosomes (unilamellar liposomal vehicles incorporating influenza haemagglutinin), AS04 ([SBAS4] Al salt with MPL), ISCOMS (structured complex of saponins and lipids), polylactide co-glycolide (PLG), microbial derivatives (natural and synthetic), e.g., monophosphoryl lipid A (MPL), 3D-MPL and β(1-6) glucosamine disaccharides, Detox (MPL+*M. phlei* cell wall skeleton), AGP [RC-529] (synthetic acylated monosaccharide), DC_Chol (lipoidal immunostimulators able to self-organize into liposomes), OM-174 (lipid A derivative), 3-O-deacylated monophosphoryl lipid A, 3-O-deacylated diphosphoryl lipid A, CpG motifs (synthetic oligonucleotides containing immunostimulatory CpG motifs), modified LT and CT (genetically modified bacterial toxins to provide non-toxic adjuvant effects), endogenous human immunomodulators (e.g., hGM-CSF (granulocyte macrophage colony-stimulating factor), cytokines (e.g., IL-2, IL-7, IL-12, hIL-12, TNF-alpha, and IFN-gamma (e.g., cytokines that can be administered either as protein or plasmid encoded), imidazoquinoline immune response modifier (e.g., resiquimod, imiquimod and gardiquimod), double stem loop immune modifier (dSLIM), Immudaptin (C3d tandem array)), plant alkaloids (e.g., tomatine), inert vehicles (e.g., gold particles), glycopyranosyl lipid adjuvant, adjuvant emulsion systems based on squalene, α-tocopherol, and polyoxyethylene sorbitan monooleate (TWEEN-80), and optionally immunostimulant QS21 and optionally 3D-MPL, and combinations thereof.

Useful emulsion immunologic adjuvants include, e.g., Complete Freund's Adjuvant (CFA), which is an oil in water emulsion that includes heat-killed mycobacteria, Incomplete Freund's Adjuvant (IFA), which is an oil in water emulsion that does not include mycobacteria, MF59, which is a water in oil squalene-based emulsion, and AS03, which is an oil in water adjuvant emulsion that includes α-tocopherol, squalene and polysorbate 80.

Useful microparticle immunologic adjuvants include, e.g., virus-like particles (VLP), which are formed from structural viral proteins (including enveloped and nonenveloped VLPs), virosomes that include reconstituted viral envelopes with membrane lipids and viral glycoproteins, virosomal HA and sialic acid, polylactic acid, polylactic acid/poly(lactic-coglycolic acid) microparticles, and combinations thereof.

Useful immunologic adjuvants include, e.g., anti-CD40 (cluster of differentiation 40), PD-1 (programmed cell death protein 1) path inhibitors, anti CTLA-4 (cytotoxic T-lymphocyte-associated protein 4) monoclonal antibodies, and Fms-related tyrosine kinase 3 (FLT3) ligand.

Useful immunologic adjuvants are commercially available under a variety of trade designations including, e.g., the ALHYDROGEL trade designation from InvivoGen (San Diego, Calif.) including ALHYDROGEL ADJUVANT 2% aluminum hydroxide wet gel suspension.

The hyper-allergenic composition includes at least 0.0001% by weight, no greater than 20% by weight, at least 0.1% by weight, no greater than 10% by weight, from 1% by weight to 5% by weight, or even from 2% by weight to 5% by weight immunologic adjuvant.

Carrier

The carrier is suitable for topical delivery of the immunogenic agents to the individual. The carrier can vary, as desired. Useful carriers include, e.g., liquids (e.g., lotions (e.g., liquids containing insoluble material in the form of a suspension or emulsion, intended for external application, including spray lotions) and aqueous solutions), semi-solid compositions (e.g., gels (colloids in which the disperse phase has combined with the dispersion medium to produce a semisolid material, e.g., a jelly), creams (e.g., soft solids and viscous liquids), ointments (soft, unctuous preparations)), and solid formulations (e.g., topical patches). The carrier can be in a variety of forms including, e.g., an emulsion (e.g., an oil-in-water (O/W) emulsion, a water in-oil (W/O) emulsion), a suspension, a milk preparation, an ointment, serum, powder, spray, aerosol, stick, and combinations thereof. The carrier preferably is water-based. The carrier optionally includes an emulgent to prevent separation of the oil phase and the water phase, where these phases are present.

Useful carriers include, e.g., emollients, humectants, gelling agents (e.g., polyacrylic acid polymers and hydroxy ethyl acrylate copolymers, starch, starch derivatives, cellulose derivatives, polyvinylpyrrolidone, polyethylene oxide, polyvinyl alcohol, and combinations thereof), emulsifying agents (e.g., glyceryl stearate, sorbitan monostearate, cetyl alcohol, dimethyl isosorbide, and combinations thereof), polyethylene glycol (PEG), mineral oil, glycerol, glycerin, glyceryl monocaprylate, paraffin, paraffin oil, squalene oil, squalane, petrolatum, petroleum jelly, oils of plant origin (e.g., jojoba oil, sesame oil, rapeseed oil, castor oil, soybean oil, palm oil, coconut oil, olive oil, sunflower oil, and nut oil (e.g., almond oil)), synthetic oils (e.g., fatty esters, e.g., purcellin oil, 2-ethylhexyl palmitate, 2-octyldodecyl stearate, 2-octyldodecyl erucate, isostearyl isostearate, 2-octyldodecyl benzoate, and hydrogenated isoparaffin), triglycerides of caprylic/capric acids, octyldodecanol, isohexadecane, petrolatum, lanolin, anhydrous lanolin, and combinations thereof.

The carrier can be manufactured using a variety of methods. One useful method includes dispersing hydrophobic components (e.g., emollients, lubricants, and antigens) in an oil phase optionally with blending agents and thickening agents, dispersing or dissolving hydrophilic components (e.g., perfumes, colors and preservatives) in an aqueous phase, and the combining the oil phase and the water phase with mixing.

The method of manufacturing the carrier may have several steps including adding solid ingredients to the oil phase, dispersing active ingredients, preparing the water phase by adding emulsifiers, stabilizers and combinations thereof to the water phase, mixing the oil and water to form an emulsion, and optionally heating to the composition to from 110° F. to 185° F. (from 45° C. to 85° C.) to achieve a desired composition and viscosity.

The carrier can be an existing skin cream and the allergen(s) can be mixed with the existing skin cream. Preferably the skin cream is substantially free of, or even free of, growth factor.

The amount of carrier required for a single application can vary depending upon the patient and desired outcome. Useful compositions include at least 1% by weight to 95% by weight, from 1% by weight to 90% by weight, or even from 5% by weight to 95% by weight carrier based on the weight of the composition.

Other Ingredients

The hyper-allergenic composition optionally includes other ingredients including, e.g., penetration enhancers, preservatives, antioxidants, surfactants, thickening agents, stiffening agents, viscosity enhancers, film formers, additional gelling agents, foam formers, stabilizers, buffering agents, pH adjusting agents, suspending agents, stabilizing agents, solvents (organic solvents), co-solvents, water, crystal growth inhibitors, diluents, chelating agents, propellants, coloring agents (e.g., dyes and pigments), perfumes, non-allergenic proteins, and combinations thereof. Useful non-allergenic proteins and components are disclosed, e.g., in Spenser, U.S. Pat. No. 7,306,810 and McElwain, U.S. Pat. No. 6,261,603, both of which are incorporated herein by reference.

Penetration enhancers act by various mechanisms to reduce the skin barrier and accelerate absorption of the allergen and optionally the immunologic adjuvant through the skin. Useful penetration enhancers include, e.g., sulphoxides (e.g., dimethylsulphoxide (DMSO)), dodecyl methyl sulfoxide, Azones (e.g., 1-butyl-2-azacycloheptanones, 1-hexyl-2-azacycloheptanones, 1-octyl-2-azacycloheptanones, and 1-dodecylazacycloheptan-2-one (Laurocapram)), pyrrolidones (e.g., 1-ethyl-2-pyrrolidone, 1-butyl-2-pyrrolidones, 1-hexyl-2-pyrrolidinone, 1-octyl-2-pyrrolidinone, 1-decyl-2-pyrrolidinone, 1-dodecyl-2-pyrrolidinone, N-methyl-2-pyrrolidone, and 2-pyrrolidone), alcohols (e.g., 1-butanol, 1-pentanol, 1-hexanol, 1-octanol, benzyl alcohol, 2-phenylethanol, ethanol, isopropyl alcohol, decanol, caprylic alcohol, hexylene glycol, and butylene glycol), dioxolane derivatives (e.g., 2-(1-butyl)-2-methyl-1,3 dioxolane, 2-(1-hexyl)-2-methyl-1,3 dioxolane, and 2 N-nonyl-1,3-dioxolanes), fatty acids (e.g., decanoic acid, undecanoic acid, lauric acid, tridecanoic acid, myristic acid, pentadecanoic acid, palmitic acid, stearic acid, linoleic acid, oleic acid, ricinoleic acid, lauric acid, myristic acid and capric acid), surfactants (e.g., sodium lauryl sulfate, cetyltrimethyl amonium bromide, sorbitan monolaurate, polysorbate 80, dodecyl dimethyl ammoniopropane sulfate, polyoxyethylene-2-oleyl ether, and polyoxy ethylene-2-stearyl ether), terpenes (e.g., thymol, menthol, menthone, carvacrol, and cineole), limonene, urea, sorbitol, mannitol, oligosaccharides, benzyl benzoate, dimethyl isosorbide, monooleate of ethoxylated glycerides (having from 8 to 10 ethylene oxide units), alpha-tocopherol polyethylene glycol succinate (vitamin E-TPGS), transcutol (diethylene glycol monoethyl ether), glycofurol (tetrahydrofurfuryl alcohol PEG ether), caprylocaproyl macrogol-8 glycerides (labrasol), and mixtures thereof. The optional penetration enhancer can be present in the composition in an amount of from 1% by weight to 50% by weight of the composition, or even from 1% by weight to 40% by weight of the composition.

Useful surfactants include, e.g., anionic, cationic, non-ionic, zwitterionic and amphoteric surfactants and combinations thereof including, e.g., polysorbate 60, polyethylene glycol (15)-hydroxy stearate, anionic surfactants such as sodium lauryl sulfate, ammonium lauryl sulfate, sodium lauryl ether sulfate, triethylamine lauryl sulfate, triethanolamine lauryl sulfate, monoethanolamine lauryl sulfate, docusate sodium, potassium lauryl sulfate; cationic surfactants such as cetrimonium bromide, benzalkonium chloride, stearyl dimethylbenzyl ammonium chloride, and combinations thereof; non-ionic surfactants such as fatty alcohols, cetyl alcohol, stearyl alcohol, cetostearyl alcohol, oleyl alcohol, polyoxyethylene glycol sorbitan alkyl esters (Polysorbate, Tween), sorbitan alkyl esters (Spans), sorbitan monostearate, stearic acid, block copolymers of polyethylene glycol and polypropylene glycol (Poloxamers), polyoxyethylene lauryl amine, PEG-distearate, PEG-hydroxystearate, propylene glycol monostearate; polyoxyethylene glycol alkyl ethers such as polyoxyethylene butyl ether, polyoxyethylene cetyl ether, polyethyleneglycol cetyl/stearyl ether, polyoxyethylene oleyl cetyl ether, polyoxyethylene oleyl ether, laureth-4 and polyoxyethylene lauryl ether, and combinations thereof.

Useful solvents include, e.g., azone (e.g., 1-dodecylazacycloheptan-2-one), 2-(n-nonyl)-1,3-dioxolane, polyols (e.g., hexylene glycol, diethylene glycol, and propylene glycol), n-alkanols, terpenes, di-terpenes, tri-terpenes, terpen-ols, limonene, 1-menthol, dioxolane, ethylene glycol, propylene glycol, sulfoxides (e.g., dimethylsulfoxide (DMSO), dimethylformamide, methyl dodecyl sulfoxide, dimethylacetamide, monooleates of ethoxylated glycerides having from 8 to 10 ethylene oxide units, esters (e.g., ethyl acetate, butyl acetate, methyl propionate, capric/caprylic triglycerides, octyl myristate, and dodecyl-myristate), myristyl alcohol, lauryl alcohol, lauric acid, lauryl lactate, ketones, amides (e.g., acetamide) oleates (e.g., triolein), alkanoic acids (e.g., caprylic acid), lactams (e.g., azone), dialkylamino acetates, polyethylene glycol derivatives that are liquid at room temperature (e.g., PEG-200, PEG-300, PEG-400 and PEG-600), and combinations thereof.

Useful preservatives include, e.g., benzalkonium chloride, methyl, ethyl, propyl or butyl paraben, benzyl alcohol, phenylethyl alcohol, benzethonium, chlorobutanol, phenoxy ethanol, potassium sorbate, benzoic acid, and combinations thereof.

Useful film forming agents include, e.g., hydroxypropyl methyl cellulose, hydroxypropyl cellulose, polyvinyl pyrrolidone, gelatin, polyethylene oxide, hydroxyethyl cellulose, sodium alginate, and combinations thereof.

Useful crystal growth inhibitors include, e.g., hydroxypropyl methylcellulose, hydroxypropyl methylcellulose acetate succinate, carboxymethyl cellulose acetate butyrate, poly(vinyl pyrrolidinone), poly(vinyl pyrrolidinone-vinyl acetate), cellulose acetate adipate propionate, cellulose acetate phthalate, hydroxypropylmethylcellulose phthalate, cellulose acetate suberate, cellulose acetate sebacate, polyethylene glycol, and combinations thereof.

Useful additional gelling agents include, e.g., sugars, sugar derived alcohols, silicon dioxide, and combinations thereof.

The hyper-allergenic composition optionally is substantially free of, or even free of, a growth factor. Growth factors are polypeptides that stimulate cell proliferation and are major growth-regulatory molecules for cells in vivo. Examples of growth factors include transforming growth factors, epidermal growth factors, insulin-like growth factors, platelet-derived growth factor, and fibroblast growth factors.

Preparation

The hyper-allergenic composition can be prepared using any suitable method including, e.g., adding the components to a mixer in an order of addition from the ingredient present at the greatest concentration to the ingredient present in the smallest amount. In one useful method of making the hyper-allergenic composition, the allergen is added last. Examples of useful mixing procedures are described in U.S. Pat. No. 10,238,686 (Ganga, Sr.) and incorporated herein.

The hyper-allergenic composition has a pH of from 5 to 10, from 6 to 9, or even from 5.5 to 7.5.

The hyper-allergenic composition preferably is thixotropic and has a viscosity from 1,000 centipoise (cP) to 20,000 cP, from 5,000 cP to 15,000 cP, or even from 9,000 cP to 12,000 cP at 77° Fahrenheit (25° Centigrade).

Packaging

The topical hyper-allergenic composition can be stored in and dispensed from any suitable packaging material. Useful packaging materials include, e.g., packets (e.g., metal foil, polymeric, paper, multilayer packets, blister packs, and combinations thereof), tubes (e.g., metal foil, polymeric, paper, and multilayer tubes, and sealable and resealable tubes), bottles (e.g., glass and polymeric bottles), tubs, vials (e.g., metal, glass and polymeric vials), wipes, and combinations thereof, and can be equipped with a variety of applicators including, e.g., pump applicators, spray applicators, brush applicators, and sponge applicators. Useful packaging materials are described, for example, in U.S. Pat. No. 7,819,251 (West, et al.), which is incorporated herein by reference.

Method of Treatment

The hyper-allergenic composition is applied on, and preferably rubbed into, the skin of an individual (e.g., a patient with cancer). Preferably the hyper-allergenic composition is applied to the area of the skin, or a part of the body, that includes relatively thin skin. Particularly useful application areas include the skin found in the area of, e.g., the wrists, the underarms, behind the knees, under the eyes, eyelids, the back of the hands (i.e., dorsal side of the hand), arms, legs, neck ears, face and combinations thereof. The hyper-allergenic composition optionally is applied to the individual's skin repeatedly over a period of time (e.g., hours, days, weeks, months, years and combinations thereof) to provide the individual with continuous exposure to the immunologic agents. The hyper-allergenic composition also can be applied to multiple areas of the skin simultaneously or sequentially.

The method optionally includes monitoring the level of at least one type of IgE antibody in the individual's blood. Any suitable method of monitoring and measuring the level of IgE in the blood can be used. One suitable method of measuring the blood levels of IgE antibodies includes measuring the total serum IgE concentration by a radioimmunosorbent test. One useful radioimmunosorbent test is commercially available from Phadebas RIST, Pharmacia. Although variations in the upper limit of normal total serum IgE have been reported (e.g., the upper limit of normal total serum IgE has been reported as ranging from 150 UI/ml to 1,000 UI/ml), the accepted upper limit is from 150 UI/ml to 300 UI/ml. The blood serum IgE concentration is measured before and after exposure to the hyper-allergenic composition. An increased serum IgE concentration after exposure to the hyper-allergenic composition corresponds to an immunologic response to the allergenic stimulant.

In some methods of treatment, the hyper-allergenic composition induces atopy with symptoms ranging from mild to severe, including such symptoms as hives, welts, swelling of affected area, runny nose, sneezing, headache, reddened, itchy, or teary eyes, sore throat with hoarse voice, abdominal cramps, chest tightness, wheezing with shortness of breath, anaphylactic shock, and combinations thereof.

Optionally, at least one antihistamine is used to relieve some of the allergy symptoms associated with the hyper-allergenic composition. Useful antihistamines include: Brompheniramine (Dimetane); Cetirizine (Zyrtec); Chlorpheniramine (ChlorTrimeton); Clemastine (Tavist); Diphenhydramine (Benadryl); Fexofenadine (Allegra); and Loratadine (Alavert, Claritin). Blocking the production of histamines with antihistamines may inhibit some forms of cancer (e.g., melanoma growth). The antihistamines may be used before, during, or after the hyper-allergenic composition has been applied.

In the event a cancer patient becomes dangerously allergic to the inventive skin-cream formulation wherein the main adverse effect is anaphylaxis, administration of epinephrine (e.g., EpiPen) may be used to alleviate an anaphylaxis emergency.

Optionally, a recombinant DNA-derived humanized IgG1k monoclonal antibody (e.g., Omalizumab) can be used to reduce sensitivity to the hyper-allergenic composition.

The method of treatment optionally includes administering at least one complementary therapy before, during or after application of the composition. Useful complementary therapies include, e.g., acupuncture, massage, aromatherapy, and combinations thereof.

Although the hyper-allergenic composition has been described as a topical skin composition such as a skin cream, the hyper-allergenic composition can be in a variety of forms including, e.g., other personal products including cosmetics (e.g., lipstick and make-up), antiperspirants, deodorants, perfumes, soaps, bath oils, feminine care products, oral hygiene products, depilatories, shampoos, conditioners, after-shave lotions, shave-conditioning formulations, sunscreens, and combinations thereof.

The topical hyper-allergenic composition can be used during any stage of cancer and is suitable for treating any type of cancer including, e.g., cervical cancer, ovarian cancer, breast cancer, prostate cancer, fibrosarcoma, myxosarcoma, liposarcoma, chondrosarcoma, osteogenic sarcoma, chordoma, angiosarcoma, endotheliosarcoma, lymphangiosarcoma, pseudomyxoma petitonei, lymphangioendotheliosarcoma, synovioma, mesothelioma, Ewing's tumor, leiomyosarcoma, rhabdomyosarcoma, colon carcinoma, pancreatic cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oliodendroglioma, meningioma, melanoma, neuroblastoma, retinoblastoma, leukemia, lymphoma, multiple myeloma, Waldenstrom's macroglobulinemia and heavy chain disease, and combinations thereof.

The topical hyper-allergenic composition can also be used in combination with other cancer treatments and therapies.

In another embodiment, a healthy person (the subject) is exposed to the hyper-allergenic composition so as to generate an immune response in the subject. Serum antibodies are then isolated from the subject's blood and then be injected into a cancer patient for whom specific immunity is desired.

Although the hyper-allergenic composition has been described as being a useful treatment for cancer, the composition also is suitable as a therapeutic treatment for autoimmune diseases (e.g., rheumatoid arthritis, Lupus, and Celiac disease), Sjögren's syndrome, Polymyalgia rheumatica, Ankylosing spondylitis, Type 1 diabetes, Alopecia areata, Vasculitis, Temporal arteritis, and multiple sclerosis.

The invention will now be described by way of the following examples. All parts, ratios, percentages and amounts stated in the Examples are by weight unless otherwise specified.

EXAMPLES

Test Procedures

Test procedures used in the examples include the following. All ratios and percentages are by weight unless otherwise indicated. The procedures are conducted at room temperature (i.e., an ambient temperature of from 20° C. to 25° C.) unless otherwise specified.

Example 1

A forced immunity to allergens from the rubber-tree *Hevea brasiliensis* (Hev-b) is harnessed to inhibit tumor growth and metastasizing in a patient. The over expression of the Rho family of GTPases has been shown to manifest in multiple types of cancer. Rubber elongation factor (Hev-b 1) is a cross-reactive allergen from *Hevea brasiliensis* that has structure homology with members of the Rho family of GTPases. Forced immunity to Hev-b 1 may induce the formation of IgE-primed mast cells that cross-react with members of the Rho family of GTPases, affecting angiogenesis in metastatic cancer-cells.

Example 2

The hyper-allergenic composition of Example 2 is prepared as follows: 0.1 grams (g) of rHev-b 1 (Thermo Fischer Scientific) is added to 10 g of ALHYDROGEL adjuvant 2% (InvivoGen, San Diego, California) to form a mixture having a working concentration of from 1:9 to 1:1 (ALHYDROGEL: of rHev-b 1). One gram of the mixture is added to 100 grams of EUCERIN pH 5 cream with mixing to form a uniform composition.

Example 3

The hyper-allergenic composition of Example 3 is prepared as follows: 0.1 g rHev-b 1 (allergen 1) and 0.1 g of rHev-b 3 (allergen 2) (Thermo Fischer Scientific) is added to 20 g of ALHYDROGEL aluminum hydroxide adjuvant 2% to form a mixture having a working concentration of from 1:9 to 1:1 (ALHYDROGEL: Allergens 1 and 2). One gram of the mixture is added to 100 grams of EUCERIN pH 5 cream with mixing to form a uniform composition.

Example 4

The hyper-allergenic composition of Example 3 is prepared as follows: 0.1 g rHev-b 1 is added to 0.1 g of ADDAVAX (InvivoGen) to form a mixture having a working concentration of about 1:1 (ADDAVAX:rHev-b 1). One gram of the mixture is added to 100 grams of EUCERIN pH 5 cream with mixing to form a uniform composition.

Example 5

The hyper-allergenic composition of Example 5 is prepared as follows: 0.1 g rHev-b 1 (allergen 1) and 0.1 g rHev-b 3 (allergen 2) is added to 0.2 g ADDAVAX to form a mixture having a working concentration of about 1:1 (ADDAVAX: allergens 1 and 2). One gram of the mixture is added to 100 grams of EUCERIN pH 5 cream with mixing to form a uniform composition.

Example 6

The hyper-allergenic composition of Example 6 is prepared as follows: 0.1 g rHev-b 1 is added to 100 g of EUCERIN pH 5 cream with mixing to form a uniform composition.

Other embodiments are within the claims.

What is claimed is:

1. A topical hyper-allergenic composition comprising:
    a first protein allergen that exhibits amyloid-β structure and immunogenicity in humans;
    a second protein allergen that exhibits immunogenicity in humans;
    an immunologic adjuvant; and
    a carrier,
    the hyper-allergenic composition inducing the formation of class-E immunoglobulins (IgE) and IgE-primed effector cells.

2. A method of treating cancer in a patient, the method comprising:
    applying the composition of claim 1 to the skin of the patient.

3. The method of claim 2 further comprising massaging the composition into the skin.

* * * * *

UNITED STATES PATENT AND TRADEMARK OFFICE
CERTIFICATE OF CORRECTION

| | |
|---|---|
| PATENT NO. | : 11,911,463 B2 |
| APPLICATION NO. | : 16/513334 |
| DATED | : February 27, 2024 |
| INVENTOR(S) | : Dochniak |

It is certified that error appears in the above-identified patent and that said Letters Patent is hereby corrected as shown below:

On the Title Page

Item "(72)", should read item "(75)".

Item (73) Assignee, Please Change "None" to --ALLEAMIT INC. 4503 KEITHSON DR. ARDEN HILLS, MINNESOTA 55112--.

Signed and Sealed this
Second Day of April, 2024

Katherine Kelly Vidal
*Director of the United States Patent and Trademark Office*